(12) United States Patent
Keady et al.

(10) Patent No.: US 11,985,467 B2
(45) Date of Patent: May 14, 2024

(54) HEARING SENSITIVITY ACQUISITION METHODS AND DEVICES

(71) Applicant: The Diablo Canyon Collective LLC, Wilmington, DE (US)

(72) Inventors: John Patrick Keady, Fairfax Station, VA (US); John Usher, Beer (GB)

(73) Assignee: The Diablo Canyon Collective LLC, Wilmington, DE (US)

( * ) Notice: Subject to any disclaimer, the term of this patent is extended or adjusted under 35 U.S.C. 154(b) by 0 days.

(21) Appl. No.: 17/345,566

(22) Filed: Jun. 11, 2021

(65) Prior Publication Data

US 2021/0306734 A1 Sep. 30, 2021

Related U.S. Application Data

(63) Continuation of application No. 16/419,566, filed on May 22, 2019, now Pat. No. 11,122,354.

(60) Provisional application No. 62/674,657, filed on May 22, 2018.

(51) Int. Cl.
| | | |
|---|---|---|
| H04R 1/10 | (2006.01) |
| A61B 5/12 | (2006.01) |
| G10H 1/44 | (2006.01) |
| G10L 13/00 | (2006.01) |
| H04R 5/04 | (2006.01) |
| H04R 25/00 | (2006.01) |

(52) U.S. Cl.
CPC ........... *H04R 1/1041* (2013.01); *A61B 5/123* (2013.01); *A61B 5/121* (2013.01); *G10H 1/44* (2013.01); *G10L 13/00* (2013.01); *H04R 1/1091* (2013.01); *H04R 5/04* (2013.01); *H04R 25/70* (2013.01); *H04R 2205/041* (2013.01); *H04R 2420/07* (2013.01)

(58) Field of Classification Search
CPC ...... A61B 5/123; A61B 5/121; H04R 1/1041; H04R 1/1091; H04R 2420/07; H04R 5/04; H04R 25/70; H04R 2205/041; G10H 1/44; G10L 13/00
See application file for complete search history.

(56) References Cited

U.S. PATENT DOCUMENTS

| | | |
|---|---|---|
| 3,876,843 A | 4/1975 | Moen |
| 4,054,749 A | 10/1977 | Suzuki et al. |
| 4,088,849 A | 5/1978 | Usami et al. |

(Continued)

FOREIGN PATENT DOCUMENTS

| | | |
|---|---|---|
| EP | 1519625 A2 | 3/2005 |
| EP | 2898507 | 7/2015 |

(Continued)

OTHER PUBLICATIONS

Keerio et al., "Comparative Analysis of Vowels, Diphthongs and Glides of Sindhi", Signal & Image Processing: An International Journal (SIPIJ) vol. 2, No. 4, Dec. 2011, document of 12 pages.

(Continued)

*Primary Examiner* — Carolyn R Edwards
*Assistant Examiner* — Kuassi A Ganmavo
(74) *Attorney, Agent, or Firm* — Aikin & Gallant, LLP (57) ABSTRACT

At least one exemplary embodiment is directed to a method of determining hearing loss using audio cues whose spectrum is orthogonal to each other to identify a wearer's hearing loss, and using the information to adjust audio to normal listening levels.

15 Claims, 7 Drawing Sheets

(56) References Cited

U.S. PATENT DOCUMENTS

| | | | |
|---|---|---|---|
| 4,947,440 A | 8/1990 | Bateman et al. | |
| 5,208,867 A | 5/1993 | Stites, III | |
| 5,267,321 A | 11/1993 | Langberg | |
| 5,524,056 A | 6/1996 | Killion et al. | |
| 5,903,868 A | 5/1999 | Yuen et al. | |
| 6,021,207 A | 2/2000 | Puthuff et al. | |
| 6,021,325 A | 2/2000 | Hall | |
| 6,026,361 A * | 2/2000 | Hura | G10L 25/69 704/271 |
| 6,163,338 A | 12/2000 | Johnson et al. | |
| 6,163,508 A | 12/2000 | Kim et al. | |
| 6,226,389 B1 | 5/2001 | Lemelson et al. | |
| 6,298,323 B1 | 10/2001 | Kaemmerer | |
| 6,359,993 B2 | 3/2002 | Brimhall | |
| 6,400,652 B1 | 6/2002 | Goldberg et al. | |
| 6,415,034 B1 | 7/2002 | Hietanen | |
| 6,567,524 B1 | 5/2003 | Svean et al. | |
| RE38,351 E | 12/2003 | Iseberg et al. | |
| 6,661,901 B1 | 12/2003 | Svean et al. | |
| 6,728,385 B2 | 4/2004 | Kvaloy et al. | |
| 6,748,238 B1 | 6/2004 | Lau | |
| 6,754,359 B1 | 6/2004 | Svean et al. | |
| 6,804,638 B2 | 10/2004 | Fiedler | |
| 6,804,643 B1 | 10/2004 | Kiss | |
| 6,862,558 B2 | 3/2005 | Huang | |
| 7,072,482 B2 | 7/2006 | Van Doorn et al. | |
| 7,107,109 B1 | 9/2006 | Nathan et al. | |
| 7,143,031 B1 * | 11/2006 | Ahroon | A61B 5/121 704/224 |
| 7,149,684 B1 * | 12/2006 | Ahroon | G10L 25/48 704/224 |
| 7,209,569 B2 | 4/2007 | Boesen | |
| 7,430,299 B2 | 9/2008 | Armstrong et al. | |
| 7,433,714 B2 | 10/2008 | Howard et al. | |
| 7,450,730 B2 | 11/2008 | Bertg et al. | |
| 7,477,756 B2 | 1/2009 | Wickstrom et al. | |
| 7,562,020 B2 | 6/2009 | Le et al. | |
| 7,756,285 B2 | 7/2010 | Sjursen et al. | |
| 7,778,434 B2 | 8/2010 | Juneau et al. | |
| 7,920,557 B2 | 4/2011 | Moote | |
| 8,014,553 B2 | 9/2011 | Radivojevic et al. | |
| 8,493,204 B2 | 7/2013 | Wong et al. | |
| 8,750,295 B2 | 6/2014 | Liron | |
| 9,037,458 B2 | 5/2015 | Park et al. | |
| 9,123,343 B2 | 9/2015 | Kurki-Suonio | |
| 9,135,797 B2 | 9/2015 | Couper et al. | |
| 2001/0046304 A1 | 11/2001 | Rast | |
| 2002/0106091 A1 | 8/2002 | Furst et al. | |
| 2002/0107692 A1 * | 8/2002 | Litovsky | G10L 13/00 704/E13.008 |
| 2002/0118798 A1 | 8/2002 | Langhart et al. | |
| 2003/0161097 A1 | 8/2003 | Le et al. | |
| 2003/0165246 A1 | 9/2003 | Kvaloy et al. | |
| 2003/0212466 A1 | 11/2003 | Alferness | |
| 2004/0042103 A1 | 3/2004 | Mayer | |
| 2004/0109668 A1 | 6/2004 | Stuckman | |
| 2004/0125965 A1 | 7/2004 | Alberth, Jr. et al. | |
| 2004/0190737 A1 | 9/2004 | Kuhnel et al. | |
| 2004/0196992 A1 | 10/2004 | Ryan | |
| 2004/0203351 A1 | 10/2004 | Shearer et al. | |
| 2005/0078838 A1 | 4/2005 | Simon | |
| 2005/0123146 A1 | 6/2005 | Voix et al. | |
| 2005/0288057 A1 | 12/2005 | Lai et al. | |
| 2006/0067551 A1 | 3/2006 | Cartwright et al. | |
| 2006/0083395 A1 | 4/2006 | Allen et al. | |
| 2006/0092043 A1 | 5/2006 | Lagassey | |
| 2006/0195322 A1 | 8/2006 | Broussard et al. | |
| 2006/0204014 A1 | 9/2006 | Isenberg et al. | |
| 2007/0043563 A1 | 2/2007 | Comerford et al. | |
| 2007/0086600 A1 | 4/2007 | Boesen | |
| 2007/0189544 A1 | 8/2007 | Rosenberg | |
| 2007/0291953 A1 | 12/2007 | Ngia et al. | |
| 2008/0037801 A1 | 2/2008 | Alves et al. | |
| 2008/0165988 A1 | 7/2008 | Terlizzi et al. | |
| 2008/0212789 A1 * | 9/2008 | Cronin | H04R 25/70 381/60 |
| 2009/0010456 A1 | 1/2009 | Goldstein et al. | |
| 2009/0024234 A1 | 1/2009 | Archibald | |
| 2009/0074195 A1 * | 3/2009 | Cornell | G10L 25/69 381/58 |
| 2010/0061564 A1 | 3/2010 | Clemow et al. | |
| 2010/0098262 A1 * | 4/2010 | Frohlich | H04R 25/70 381/60 |
| 2010/0296668 A1 | 11/2010 | Lee et al. | |
| 2011/0096939 A1 | 4/2011 | Ichimura | |
| 2011/0219879 A1 * | 9/2011 | Chalupper | H04R 25/70 73/585 |
| 2011/0264447 A1 | 10/2011 | Visser et al. | |
| 2011/0293103 A1 | 12/2011 | Park et al. | |
| 2011/0299709 A1 * | 12/2011 | Anderson | A61B 5/121 381/315 |
| 2011/0313315 A1 * | 12/2011 | Attias | G16Z 99/00 600/559 |
| 2013/0182862 A1 | 7/2013 | Disch | |
| 2013/0202124 A1 * | 8/2013 | Bellanova | H04R 25/70 381/60 |
| 2013/0329900 A1 | 12/2013 | Price | |
| 2014/0195227 A1 | 7/2014 | Rudzicz | |
| 2016/0104452 A1 | 4/2016 | Guan et al. | |
| 2016/0338622 A1 * | 11/2016 | Chen | A61B 5/121 |
| 2016/0367179 A1 * | 12/2016 | Upchurch, Jr. | A61B 5/162 |
| 2017/0070833 A1 * | 3/2017 | Shennib | H04R 25/50 |
| 2017/0230769 A1 * | 8/2017 | Nguyen | H04R 25/70 |
| 2018/0116565 A1 * | 5/2018 | Raz | A61B 5/486 |

FOREIGN PATENT DOCUMENTS

| | | |
|---|---|---|
| JP | 5706513 | 4/2015 |
| WO | 2006037156 A1 | 4/2006 |

OTHER PUBLICATIONS

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

Mauro Dentino, John M. McCool, and Bernard Widrow, Adaptive Filtering in the Frequency Domain, Proceedings of the IEEE, vol. 66, No. 12, Dec. 1978.

* cited by examiner

HEARING SENSITIVITY ACQUISITION METHODS AND DEVICES

CROSS-REFERENCE TO RELATED APPLICATIONS

This application is a continuation of and claims priority benefit to U.S. patent application Ser. No. 16/419,566, filed 22 May 2019, which is a non provisional of and claims priority to U.S. Pat. App. No. 62/674,657, filed 22 May 2018, the disclosure of which is incorporated herein by reference in its entirety.

FIELD OF THE INVENTION

The present invention relates in general to methods for hardware and software components of an earphone for characterizing a user's hearing sensitivities, and in particular, though not exclusively, for the hardware and software for a wired/wireless earphone system using orthogonal audio cues for detection of hearing loss.

BACKGROUND OF THE INVENTION

Roughly 14% of people between the ages of 45 and 64 having some level of hearing loss, with that level rising to over 30% for those older than 64. User's can also incur induced hearing loss by listening to music too loud or staying in loud environments beyond recommended period.

A loss of hearing usually is associated with a loss of hearing sensitivity at various frequencies, and thus for hearing assisted devices sound amplitudes within the frequency region associated with hearing loss can be increased in an audio device (e.g., earphone). Audiograms are usually used in a professional setting to determine a frequency dependent level of hearing loss of a user. Hearing sensitivity affects what a user hears, with respect to listening to music and voice (e.g., via a phone call). A method to measure the frequency dependent hearing loss of a user while using an audio device would be useful. Note that audio can be broken into temporal and spectral components as known to those of ordinary skill in the arts of audio signal processing, for example as described in "Comparative Analysis of Vowels, Diphthongs and Glides of Slindhi" Signal & Image Processing: An International Journal (SIPIJ) Vol. 2, No. 4, December 2011, the contents of which is incorporated in it's entirety.

BRIEF DESCRIPTION OF THE DRAWINGS

Exemplary embodiments of present invention will become more fully understood from the detailed description and the accompanying drawings, wherein.

ABBREVIATIONS

A2DP: Advanced Audio Distribution Profile. The Bluetooth 2.1 mode for uni-directional transfer of an audio stream in up to 2 channel stereo, either to or from the Bluetooth host, AKA "music mode".

ASM: Ambient Sound Microphone. Microphones configured to detect sound around the listener, not in the ear canal. There is one external microphone on each HearBud.

BB: Button Box. The BB contains the rev3 PCB board, housing the processors where the HearBud signals are processed, as well as the battery and SD card.

BTLE: Bluetooth low energy, AKA Bluetooth 4.0 (i.e. non-audio low baud data transfer).

CL: Cirrus Logic, the quad core DSP in the ButtonBox.

CSR: Cambridge Silicon Radio Bluetooth module, containing the Bluetooth CSR 8670 chip, antennae, RAM etc.

DE: Directional Enhancement algorithm (works like a highly directional beam former).

DFU: Device Firmware Update. To update CSR and Cirrus Logic DSP codeload using the micro-USB connection with the Windows only CSR application "DFUWizard.exe"—this process is initiated from the iOS and Android app.

ECM: Ear Canal Microphone. Digital microphone for detecting sound in the occluded ear canal of the user. The ASM and ECM are the same component model.

SPKR/ECR: Ear Canal Receiver. A "receiver" is another name for a loudspeaker: it is probably so-called due to Bells 1876 patent for "apparatus for transmitting vocal or other sounds telegraphically", where the "receiver" was the loudspeaker transducer for receiving the telegraphic signal from the far-end party.

HSP/HFP: Headset or hands-free profile mode. In this document, the names are used interchangeably: there is a technical difference, but we mean it to mean the 2-way Bluetooth classic comms. mode.

SNR: Signal-to-noise ratio.

SPKR: LoudSpeaker, this abbreviation is often used instead of ECR but refer to the same component.

DETAILED DESCRIPTION OF EXEMPLARY EMBODIMENTS

The following description of exemplary embodiment(s) is merely illustrative in nature and is in no way intended to limit the invention, its application, or uses.

Exemplary embodiments are directed to or can be operatively used on various wired or wireless audio devices (e.g., hearing aids, ear monitors, earbuds, headphones, ear terminal, behind the ear devices or other acoustic devices as known by one of ordinary skill, and equivalents). For example, the earpieces can be without transducers (for a noise attenuation application in a hearing protective earplug) or one or more transducers (e.g. ambient sound microphone (ASM), ear canal microphone (ECM), ear canal receiver (ECR)) for monitoring/providing sound. In all the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example, specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

Figure 6A:
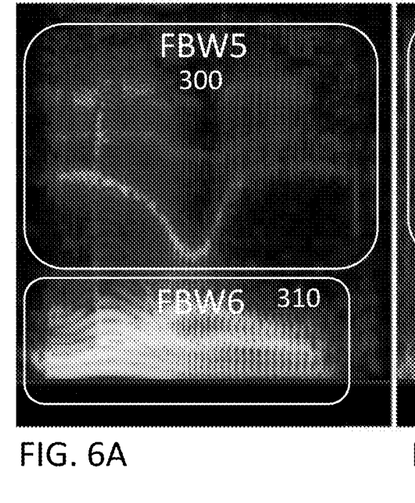
FIGS. 6A and 6B illustrates two acoustic cue's spectrograms (e.g., 300 and 310) at different loudness (e.g., sound pressure levels) and matched sound pressure levels (e.g., matching peak value sound pressure level, e.g., 320)

Acoustic cues, for example words have spectral components that have a unique pattern, like a fingerprint, that changes in time. This can be plotted as frequency versus time and is called a spectrogram. Words are typically spoken with temporal serial manner, basically one after the other in time. They are not spoken at exactly the same time unless there are two speakers. However because each has different frequency components, one can combine the words so that they are played at the same time frame, noting that some words are drawn out, some shorter. However, if we make them the same temporal length and combine, then we could detect frequency sensitivities (e.g., hearing loss) at particular frequencies, based upon what word the listener indicates he hears. The various sound pressure levels (amplitudes) of the various words can be adjusted to obtain the relative levels of amplitudes related to when the user can hear the particular word. This can be used as an interactive hearing test asking a user to indicate from a list of words/sentences what they hear, and through a combination of selective words we could hone in on the frequency bands a listener has potential hearing sensitivities or hearing loss. Acoustic cues (any acoustic signal for examples, tones, music, vocalization, noise) herein are referred to as words with specific frequency bands, or frequency band words (FBW) within which most of the power spectral density lies or sound pressure level lies. For example the words "yanii" and "laurel" have spectrograms that define each word (FIG. 6A, 300, 310). The idea of at least one exemplary embodiment is to combine the words temporally so that they occur at the same time rather than temporally serial and use this information to isolate frequency dependent hearing loss or sensitivities. The amplitudes of the unheard FBW can be increased until the user recognizes the FBW. The ratio of the amplitude before adjustment and after can be used as a ratio to amplify audio content within the frequency band associated with the FBW. Note that the FBW can be frequency orthogonal in time, which can be expressed as:

$$\int F_1(f)^* F_2(f) df < \theta_{th} \qquad (1)$$

Where F1 and F2 are the spectrum for a particular time segment, for example the entire span from the start to finish of FBW1 and FBW2 respectively. The threshold, $\theta_{th}$, can be set to the background level, for example if F1 and F2 are due to background at the particular frequency bands associated with FBW1 and FBW2, then the integral of their dot product can be used as the threshold value, $\theta_{th}$. Alternatively other values can be used by those of ordinary skill in the arts.

Music tones have a rich harmonic (frequency) spectrum; sometimes called "over-tones".

The temporal change of a sound spectrum affects its timbre. In music, timbre is the generally considered to be the difference in quality of two sounds with the same perceived loudness and the same perceived pitch. For instance, the difference, timbre are those differences in qualities of violin playing the sustained note A-440 and a child singing the sustained note A-440.

The harmonic spectrum of a musical instrument is therefore a very important factor in affecting its perceived timbre.

Frequency dependent hearing loss is a temporary or permanent change in hearing sensitivity: it can be considered a partial or total inability to hear certain frequencies.

If two versions of a single instrument recording are presented to an individual; a first with a full, un-altered spectrum, and a second with a significantly altered spectrum (e.g. some frequencies attenuated), then to a normal-hearing person the two presented recordings will have a different timbre. However, if that person has significant hearing damage at the frequencies at which the instrument recording was altered, then they will not perceive a change in timbre.

Frequency dependent hearing loss of an individual can therefore be determined by processing a single recording of an instrument to significantly affect its harmonic spectrum, and noting if the individual detects a change in timbre.

Figure 1:
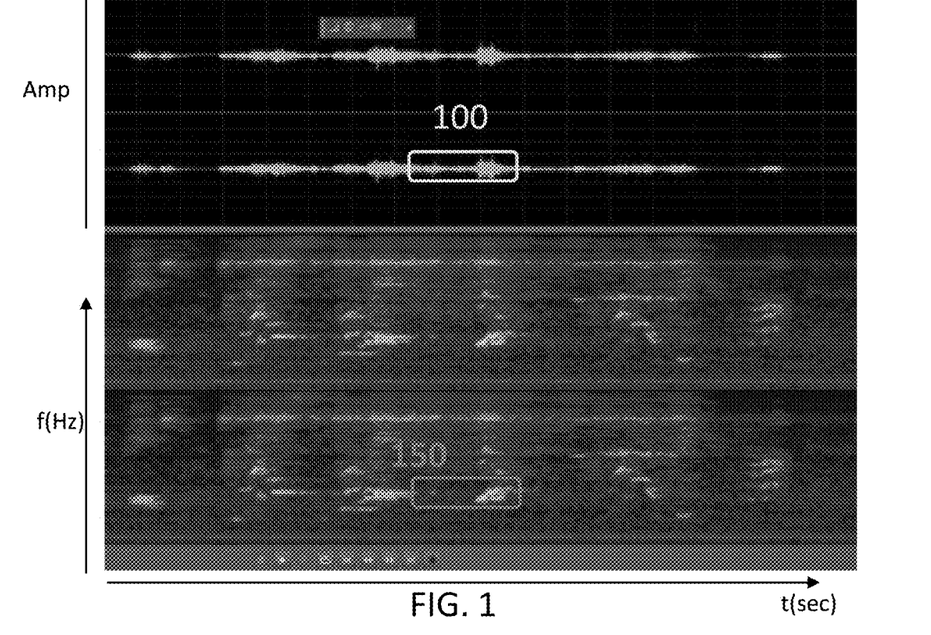
FIG. 1 illustrates two microphone channel recording with amplitude versus time and frequency versus time.

FIG. 1 illustrates two microphone channel recording with amplitude versus time (100) and frequency versus time (spectrogram) (150).

Figure 2A:
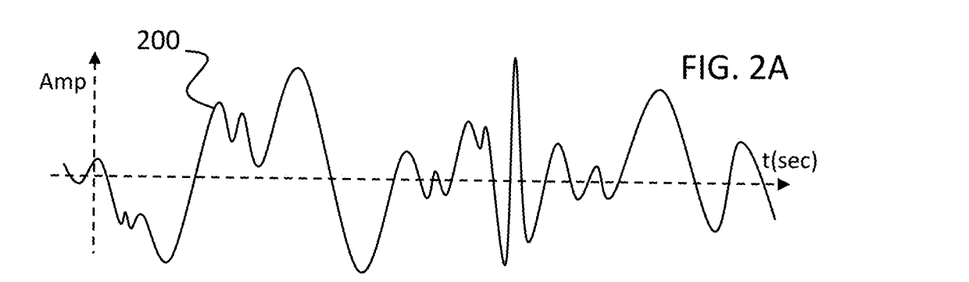
FIG. 2A and FIG. 2B illustrate an amplitude versus time plot of an acoustic cue(s) (e.g., tone, vocalization) and the associated frequency peak sweeps versus time of the acoustic cue(s)
Figure 2B:
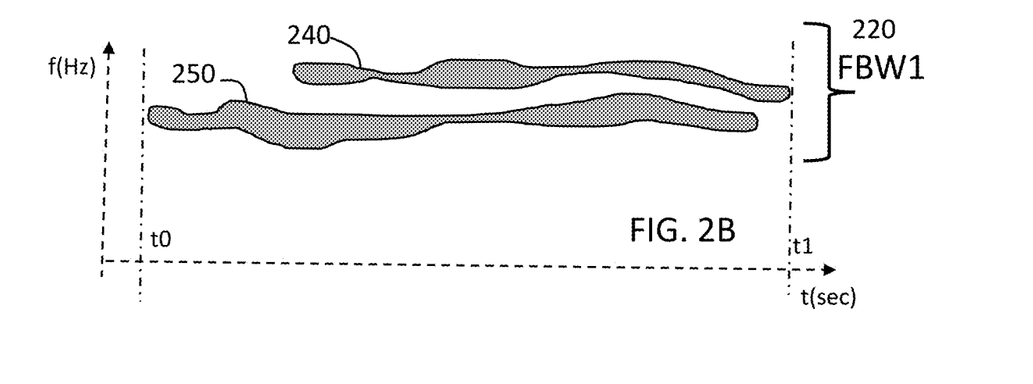

2A and FIG. 2B illustrate an amplitude versus time plot 200 of an acoustic cue(s) (e.g., tone, vocalization) and the associated frequency peak sweeps versus time 220 of the acoustic cue(s). The FBW 200 of FIG. 2A is spectrally displayed in time in FIG. 2B, as mentioned, and includes several spectral features 240 and 250 associated with FBW1 220.

Figure 3A:
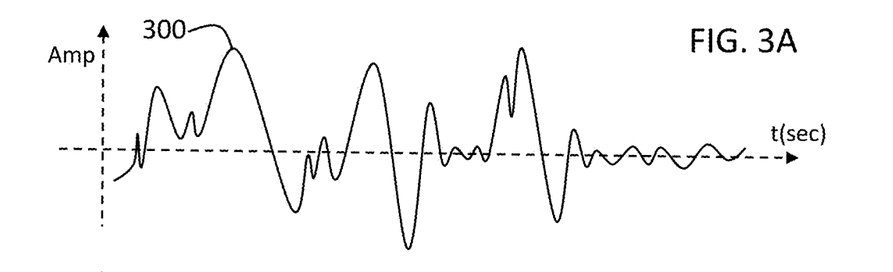
FIG. 3A and FIG. 3B illustrate an amplitude versus time plot of a second acoustic cue and the associated frequency amplitude sweeps versus time (e.g., spectrogram) of the second acoustic cue.
Figure 3B:
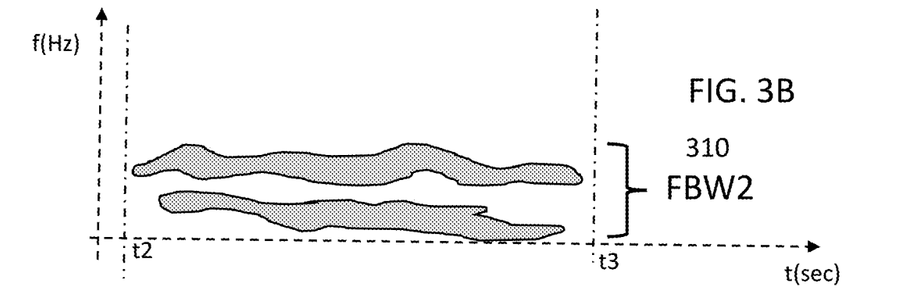
Figure 4:
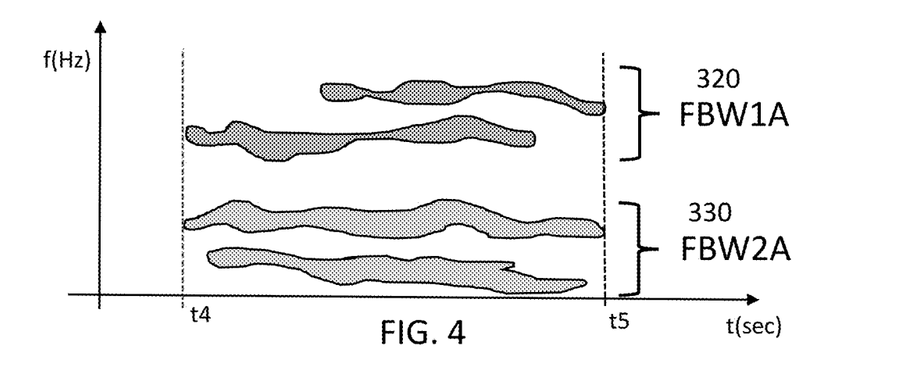
FIG. 4 illustrates a spectrogram of two acoustic cues with time matched start and end periods.
Figure 5:
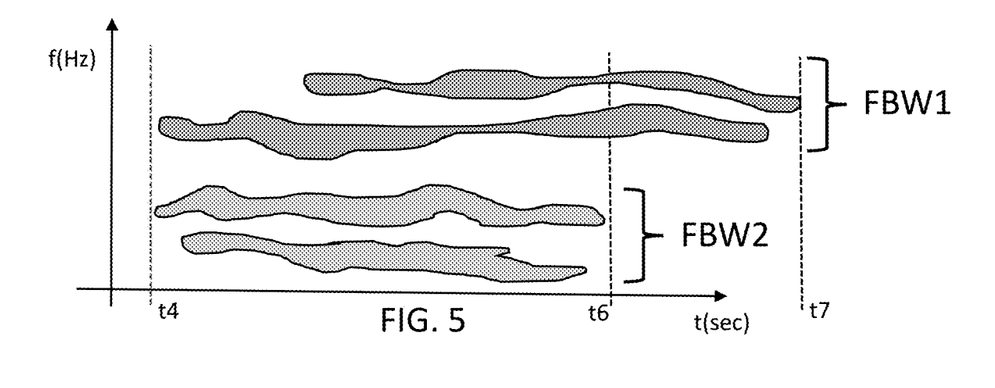
FIG. 5 illustrates a spectrogram of two acoustic cues with no modification of their temporal spectrogram extent.

FIG. 3A and FIG. 3B illustrate an amplitude versus time plot 300 of a second acoustic cue and the associated frequency amplitude sweeps versus time (e.g., spectrogram) 310 of the second acoustic cue. The acoustic cue 300 can be expressed in the spectral domain as 310 FBW2. FIG. 4 illustrates a spectrogram of FBW1 and FBW2 with time matched start and end periods FBW1A and FBW2A respectively. FIG. 5 illustrates a spectrogram of FBW1 and FBW2 with no modification of their temporal spectrogram extent. Note that, for example as in FIG. 4, if both FBW1A and FBW2A are amplitude matched (e.g., FIG. 6B) and played simultaneously, a user can then indicate which word they hear or both. The amplitude then of the non heard word can be adjusted until both are heard. This gives a ratio of modified amplitude to original amplitude, referred to herein as amplitude adjustment ratio, that can then be used to modify audio content, within the frequency band identified as associated with hearing loss, delivered to the user so that it sounds more natural to the user. Note that limits can be placed on the level of increase so that NIOSH sound level dosage values are not exceeded. Note that time matching is not needed, and instead staggered serially so that both FBW1 and FBW2 can be played serially and not simultaneously so that both are played but one after the other, and then the user asked which words they heard, and relative loudness. Hence a user interface can ask a user which sentences did the user hear, and depending upon the user indication of the words heard (e.g. selected by a dropdown menu by the user), the frequency dependency of any hearing loss can be isolated by the frequency band associated with the FBW played. The relative amplitudes of the FBW, not heard, can be adjusted and the sequence replayed until the user hears the full sentence resulting in an amplitude ratio. The relative amplitude ratios associated with the frequency bands can then be used to modify any audio delivered to the user so that the user can hear the audio as intended.

Figure 6B:
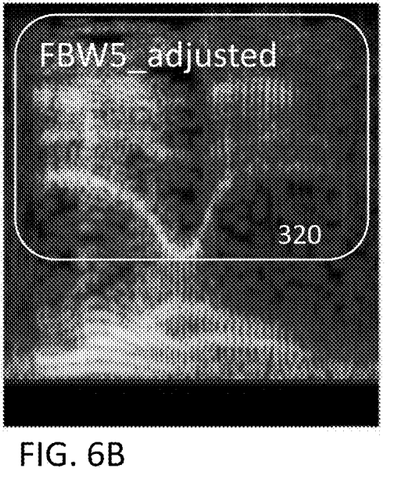

FIGS. 6A and 6B illustrates two acoustic cue's spectrograms (e.g., 300 and 310) at different loudness (e.g., sound pressure levels) and matched sound pressure levels (e.g., matching peak value sound pressure level, e.g., 320). FBW5 300 shows the spectrogram of the word "yanii" while FBW6 illustrates the spectrogram of the word "laurel", where the spectrograms do not overlap significantly. If the FBW5 and FBW6 are played simultaneously, as shown in FIG. 6, although they could also be played serially, the user can select which word they hear or a combination of both. For example if a user identifies FBW5 as being not heard its amplitude can be adjusted (e.g., FBW5_adjusted, 320) until heard, for example as it FIG. 6B. The amplitudes FBW5_adjusted can be changed until it sounds to the user the same loudness as FBW6, 310. The relative ratio amp FBW5_adjusted/FBW6 or ratio of amp FBW5_adjusted/FBW5 can be used to adjust the frequency band of any audio content.

Figure 7A:
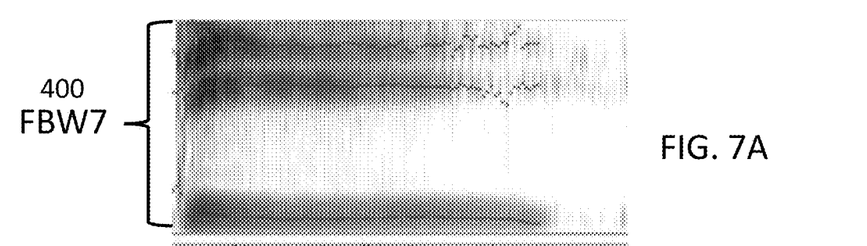
FIGS. 7A, 7B, and 7C indicate various spectrograms for various words.
Figure 7B:
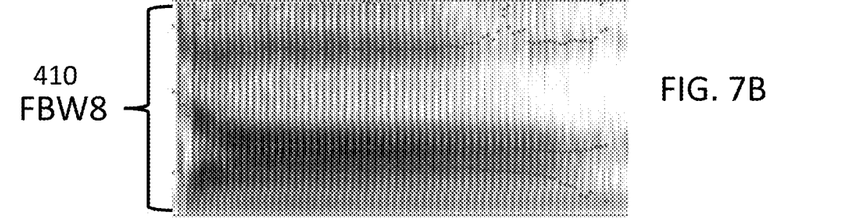
Figure 7C:
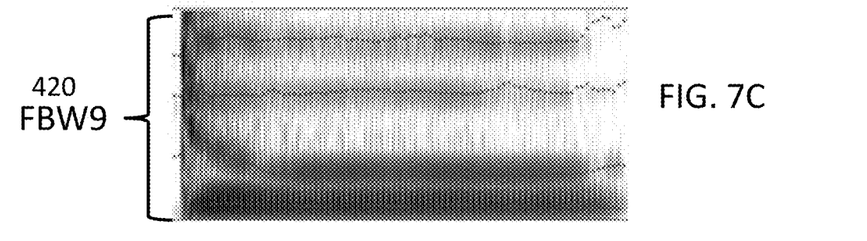

FIGS. 7A, 7B, and 7C indicate various spectrograms for the words "dee" 400 FBW7, "dah" 4100 FBW8, and "doo" 420 FBW9. Note that since these spectrums are orthogonal in frequency, they can be played simultaneously, or serially or a combination of both. Thus, a user can be asked, when all three are played, which words are heard. Note that FBWs played simultaneously can be also constructed to form different words. For example, supposed FBWA and FBWB are essentially orthogonal in frequency space. If one constructs FBWA and FBWB such that when combined a user of normal hearing hears word 1, while FWBA alone forms word 2, and FBWB alone forms word 3. A user is then asked which word they hear.

Figure 8A:
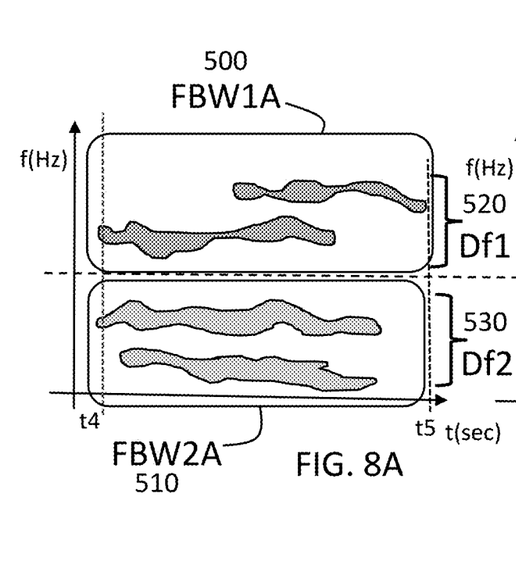
FIGS. 8A and 8B illustrate the method of isolating various frequency level of hearing loss by subsequently using new audio cues (e.g., 620 and 630) after a broader range has been determined.
Figure 8B:
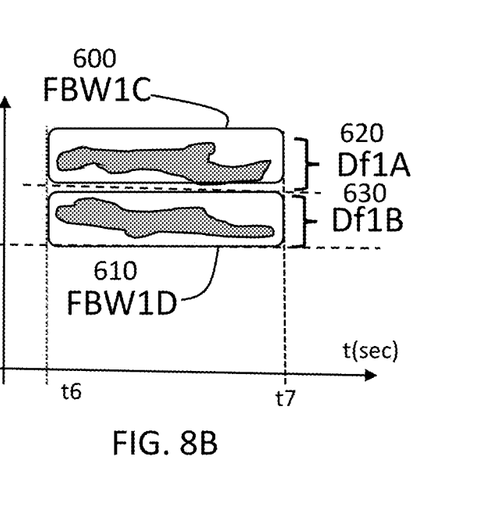

FIGS. 8A and 8B illustrate the method of isolating various frequency level of hearing loss by subsequently using new audio cues (e.g., 620 and 630) after a broader range has been determined. The first level of testing can use FBW1A 500 and FBW2A 510, to isolate the frequency band Df1 520 and Df2 530, then refinement can occur using FBW1C 600 and FBW1D 610 to isolate a more refined frequency band of hearing loss DF1A 620 and Df1B 630.

Figure 9:
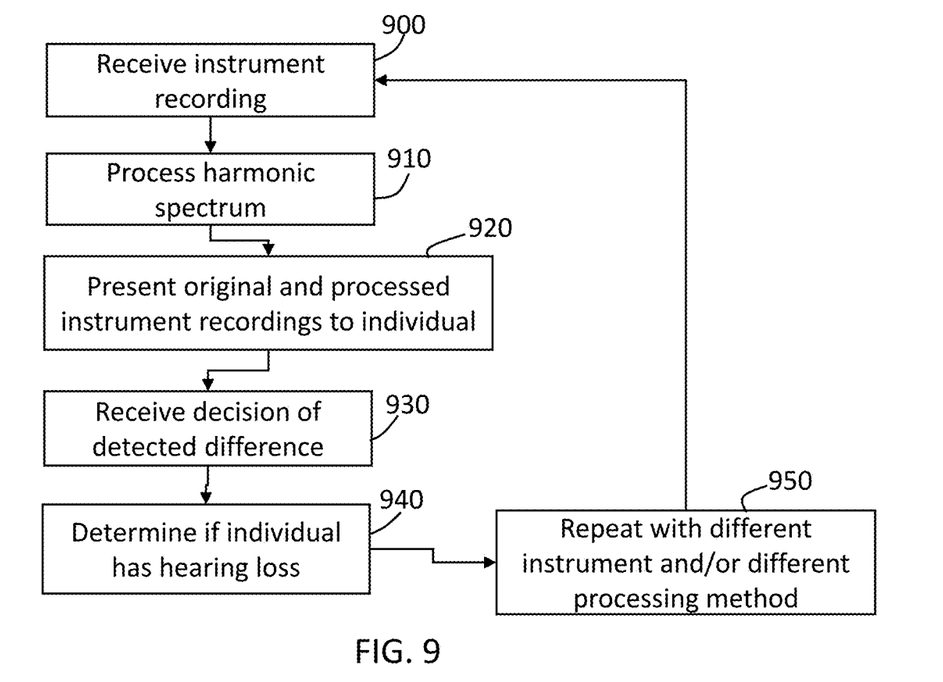
FIG. 9 illustrates a method of using musical instruments to isolate hearing loss.

FIG. 9 illustrates a method of using musical instruments to isolate hearing loss; the exemplary method comprises the following steps:

Step 1. Receive instrument audio:
Typically the instrument audio is a recording of a sustained note or drone, e.g. a violin playing the note A-440.
The recording can be received from a physical storage device e.g. a hard-drive, or can be generated procedurally (i.e. a synthesized sound).

Step 2. Process harmonic spectrum:
Typical processing involves significantly attenuating a single harmonic of the instrument, e.g., first we determine the principle fundamental harmonic, and then identify other harmonics where there is significant energy, eg the 1st, 2nd, 3rd, 4th etc. Significant energy can be defined relative to the fundamental energy, e.g. within 10 dB of the fundamental power. Identification of the frequency of each harmonic of a musical note is well known to those skilled in the art.
Attenuating the harmonic typically involves attenuation by at least 15 dB.

Step 3. Present original and processed instrument recordings to individual:
The purpose of the listening test is to determine if the individual can hear a difference in timbre between the original and processed instruments. If they can not, then this indicates hearing damage at the frequency of the modified harmonic.
The two sounds can be presented to the user via earphone or a loudspeaker.
A typical procedure to determine if a difference is heard between two sounds is the ABX test. This method is well-known for those skilled in the art.

Step 4. Receive decision of detected difference and
step 5. Determine if individual has hearing loss:
Analysis of ABX test to determine if the user can hear a difference. If the user hears no difference, then we judge the user has hearing damage at the frequency at which the original sound of step 1 was modified.

6. Repeat with different instruments and different processing methods (i.e. different frequencies of harmonic attenuation) to identify possible hearing damage at different frequencies. In a typical embodiment, we repeat the comparison test using different musical instruments and different frequency processing such that the frequency processing (i.e. harmonic attenuation) is at one third octaves between 1 kHz and 8 kHz.

Figure 10:
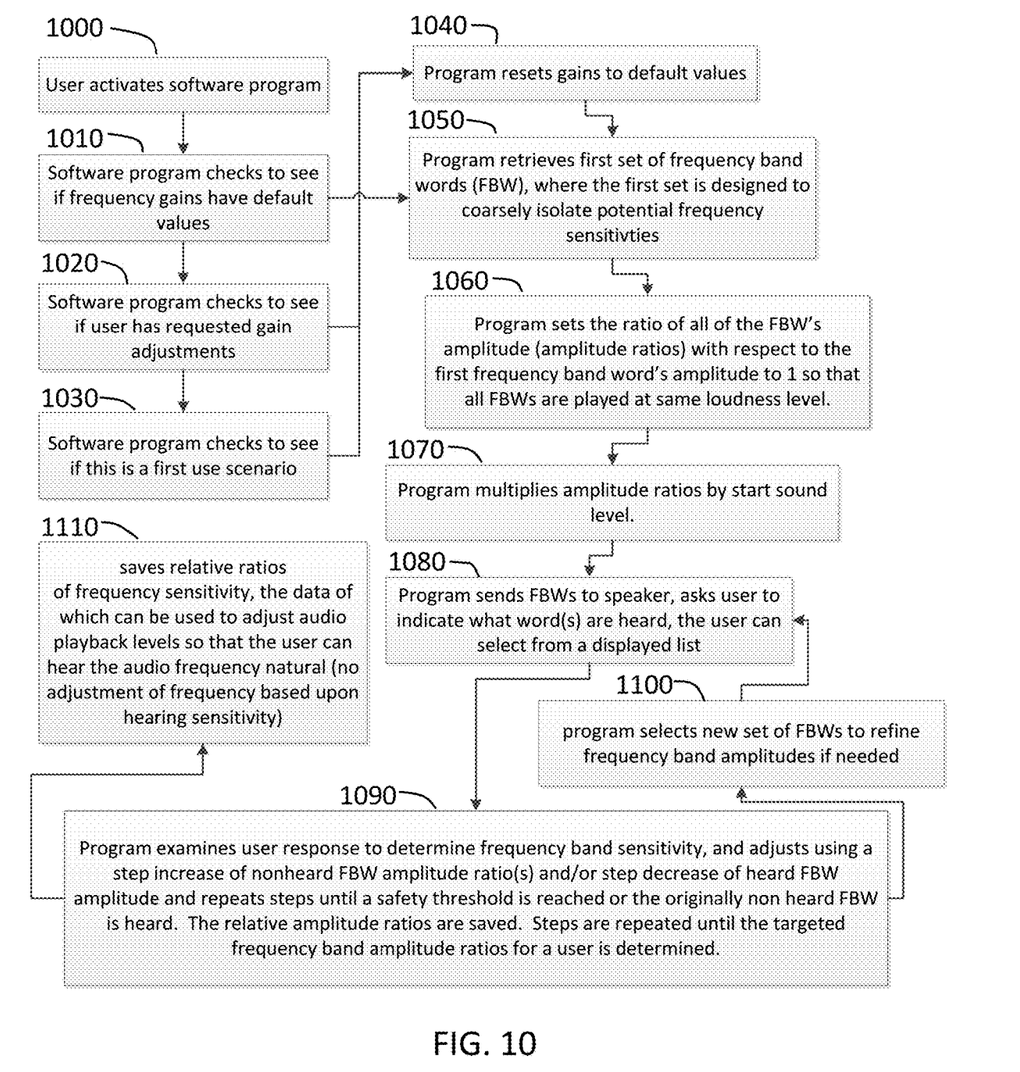
FIG. 10 a method of using overlapping and serial acoustic cues to identify hearing sensitivity levels.

FIG. 10 a method of using overlapping and serial acoustic cues to identify hearing sensitivity levels. In a first step 1000 a user activates a user interface to start the hearing sensitivity test. In step 1010, the software checks to see if there are any preset frequency gains that have been previously established, if so the gains are used initially and adjusted based upon the results of the testing. In step 1020 a check is made to see if the user indicates a noticeable loss of hearing, essentially requesting a gain. In step 1030, the program checks to see if this is the first time a user is being tested. In step 1040, the software can set gain levels to default values, for example if the program is being used for the first time for a new user. In step 1050 the system retrieves a first set of FBW where the retrieved FBW is used to determine coarse isolation of frequency dependent hear loss. At first all FBWs are played at the same loudness levels, step 1060. In step 1070 the lowest frequency FBW levels are matched to the other FBWs. The matched FBWs are sent to the speaker to play the audio to the user 1080. After acquiring the user response, the program determines frequency band sensitivity, and adjusts the amplitudes of the non heard FBWs until the user hears the words. Program examines user response to determine frequency band sensitivity, and adjusts using a step increase of nonheard FBW amplitude ratio(s) and/or step decrease of heard FBW amplitude and repeats steps until a safety threshold is reached or the originally non heard FBW is heard. The relative amplitude ratios are saved. Steps are repeated until the targeted frequency band amplitude ratios for a user is determined.

Figure 11:
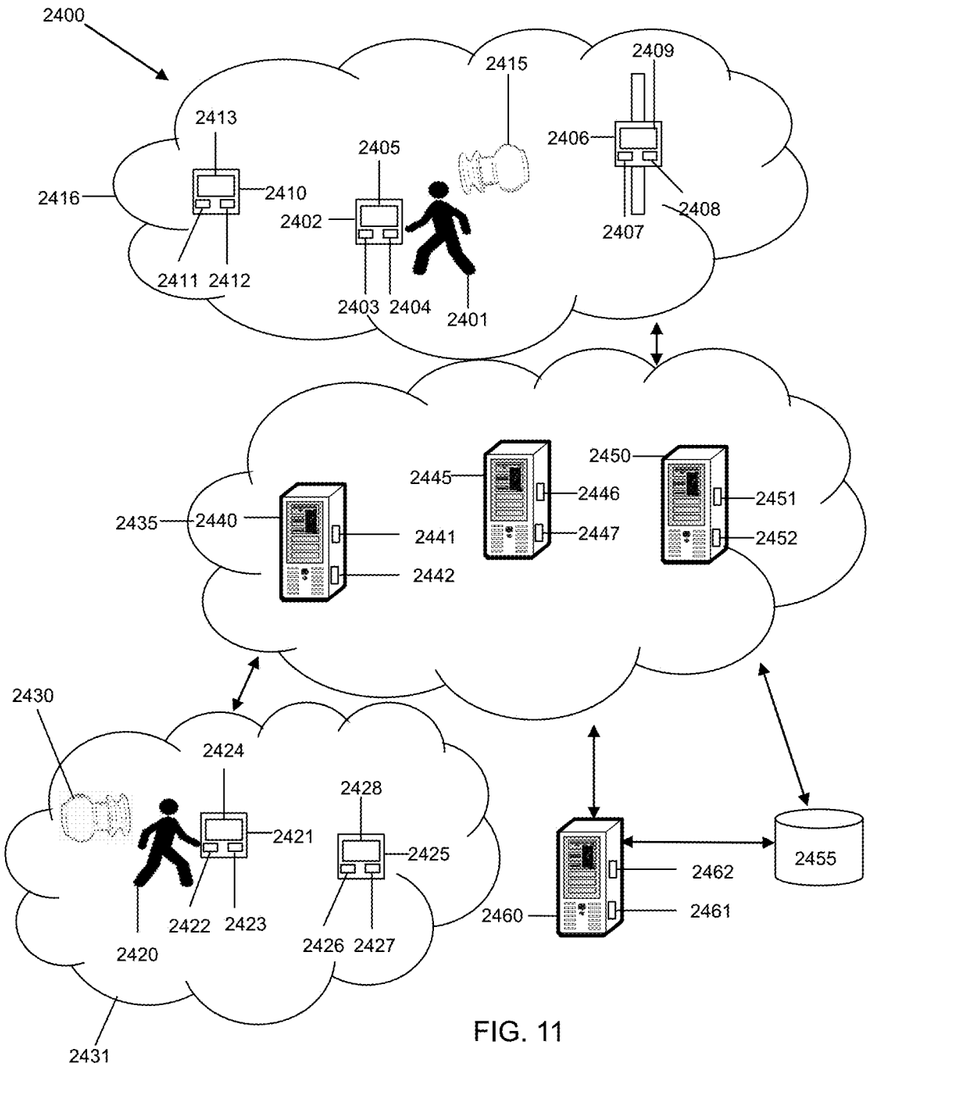
FIG. 11 is a schematic diagram of a system for utilizing earphones according to an embodiment of the present disclosure.

As shown in FIG. 11, a system 2400 and methods for utilizing eartips and/or earphone devices are disclosed. The system 2400 may be configured to support, but is not limited to supporting, data and content services, audio processing applications and services, audio output and/or input applications and services, applications and services for transmitting and receiving audio content, authentication applications and services, computing applications and services, cloud computing services, internet services, satellite services, telephone services, software as a service (SaaS) applications, platform-as-a-service (PaaS) applications, gaming applications and services, social media applications and services, productivity applications and services, voice-over-internet protocol (VoIP) applications and services, speech-to-text translation applications and services, interactive voice applications and services, mobile applications and services, and any other computing applications and services. The system may include a first user 2401, who may utilize a first user device 2402 to access data, content, and applications, or to perform a variety of other tasks and functions. As an example, the first user 2401 may utilize first user device 2402 to access an application (e.g. a browser or a mobile application) executing on the first user device 2402 that may be utilized to access web pages, data, and content associated with the system 2400. In certain embodiments, the first user 2401 may be any type of user that may potentially desire to listen to audio content, such as from, but not limited to, a music playlist accessible via the first user device 2402, a telephone call that the first user 2401 is participating in, audio content occurring in an environment in proximity to the first user 2401, any other type of audio content, or a combination thereof. For example, the first user 2401 may be an individual that may be participating in a telephone call with another user, such as second user 2420.

The first user device 2402 utilized by the first user 2401 may include a memory 2403 that includes instructions, and a processor 2404 that executes the instructions from the memory 2403 to perform the various operations that are performed by the first user device 2402. In certain embodiments, the processor 2404 may be hardware, software, or a combination thereof. The first user device 2402 may also include an interface 2405 (e.g. screen, monitor, graphical user interface, etc.) that may enable the first user 2401 to interact with various applications executing on the first user device 2402, to interact with various applications executing within the system 2400, and to interact with the system 2400 itself. In certain embodiments, the first user device 2402 may include any number of transducers, such as, but not limited to, microphones, speakers, any type of audio-based transducer, any type of transducer, or a combination thereof. In certain embodiments, the first user device 2402 may be a computer, a laptop, a tablet device, a phablet, a server, a mobile device, a smartphone, a smart watch, and/or any other type of computing device. Illustratively, the first user device 2402 is shown as a mobile device in FIG. 11. The first user device 2402 may also include a global positioning system (GPS), which may include a GPS receiver and any other necessary components for enabling GPS functionality, accelerometers, gyroscopes, sensors, and any other componentry suitable for a mobile device.

In addition to using first user device 2402, the first user 2401 may also utilize and/or have access to a second user device 2406 and a third user device 2410. As with first user device 2402, the first user 2401 may utilize the second and third user devices 2406, 2410 to transmit signals to access various online services and content. The second user device 2406 may include a memory 2407 that includes instructions, and a processor 2408 that executes the instructions from the memory 2407 to perform the various operations that are performed by the second user device 2406. In certain embodiments, the processor 2408 may be hardware, software, or a combination thereof. The second user device 2406 may also include an interface 2409 that may enable the first user 2401 to interact with various applications executing on the second user device 2406 and to interact with the system 2400. In certain embodiments, the second user device 2406 may include any number of transducers, such as, but not limited to, microphones, speakers, any type of audio-based transducer, any type of transducer, or a combination thereof. In certain embodiments, the second user device 2406 may be and/or may include a computer, any type of sensor, a laptop, a set-top-box, a tablet device, a phablet, a server, a mobile device, a smartphone, a smart watch, and/or any other type of computing device. Illustratively, the second user device 2402 is shown as a smart watch device in FIG. 11.

The third user device 2410 may include a memory 2411 that includes instructions, and a processor 2412 that executes the instructions from the memory 2411 to perform the various operations that are performed by the third user device 2410. In certain embodiments, the processor 2412 may be hardware, software, or a combination thereof. The third user device 2410 may also include an interface 2413 that may enable the first user 2401 to interact with various applications executing on the second user device 2406 and to interact with the system 2400. In certain embodiments, the third user device 2410 may include any number of transducers, such as, but not limited to, microphones, speakers, any type of audio-based transducer, any type of transducer, or a combination thereof. In certain embodiments, the third user device 2410 may be and/or may include a computer, any type of sensor, a laptop, a set-top-box, a tablet device, a phablet, a server, a mobile device, a smartphone, a smart watch, and/or any other type of computing device. Illustratively, the third user device 2410 is shown as a smart watch device in FIG. 11.

The first, second, and/or third user devices 2402, 2406, 2410 may belong to and/or form a communications network 2416. In certain embodiments, the communications network 2416 may be a local, mesh, or other network that facilitates communications among the first, second, and/or third user devices 2402, 2406, 2410 and/or any other devices, programs, and/or networks of system 2400 or outside system 2400. In certain embodiments, the communications network 2416 may be formed between the first, second, and third user devices 2402, 2406, 2410 through the use of any type of wireless or other protocol and/or technology. For example, the first, second, and third user devices 2402, 2406, 2410 may communicate with one another in the communications network 2416, such as by utilizing Bluetooth Low Energy (BLE), classic Bluetooth, ZigBee, cellular, NFC, Wi-Fi, Z-Wave, ANT+, IEEE 802.15.4, IEEE 802.22, ISA100a, infrared, ISM band, RFID, UWB, Wireless HD, Wireless USB, any other protocol and/or wireless technology, satellite, fiber, or any combination thereof. Notably, the communications network 2416 may be configured to communicatively link with and/or communicate with any other network of the system 2400 and/or outside the system 2400.

The system 2400 may also include an earphone device 2415, which the first user 2401 may utilize to hear and/or audition audio content, transmit audio content, receive audio content, experience any type of content, process audio content, adjust audio content, store audio content, perform any type of operation with respect to audio content, or a combination thereof. The earphone device 2415 may be an earpiece, a hearing aid, an ear monitor, an ear terminal, a behind-the-ear device, any type of acoustic device, or a combination thereof. The earphone device 2415 may include any type of component utilized for any type of earpiece. In certain embodiments, the earphone device 2415 may include any number of ambient sound microphones that may be configured to capture and/or measure ambient sounds and/or audio content occurring in an environment that the earphone device 2415 is present in and/or is proximate to. In certain embodiments, the ambient sound microphones may be placed at a location or locations on the earphone device 2415 that are conducive to capturing and measuring ambient sounds occurring in the environment. For example, the ambient sound microphones may be positioned in proximity to a distal end (e.g. the end of the earphone device 2415 that is not inserted into the first user's 2401 ear) of the earphone device 2415 such that the ambient sound microphones are in an optimal position to capture ambient or other sounds occurring in the environment. In certain embodiments, the earphone device 2415 may include any number of ear canal microphones, which may be configured to capture and/or measure sounds occurring in an ear canal of the first user 2401 or other user wearing the earphone device 2415. In certain embodiments, the ear canal microphones may be positioned in proximity to a proximal end (e.g. the end of the earphone device 2415 that is inserted into the first user's 2401 ear) of the earphone device 2415 such that sounds occurring in the ear canal of the first user 2401 may be captured more readily.

The earphone device 2415 may also include any number of transceivers, which may be configured transmit signals to and/or receive signals from any of the devices in the system 2400. In certain embodiments, a transceiver of the earphone device 2415 may facilitate wireless connections and/or transmissions between the earphone device 2415 and any device in the system 2400, such as, but not limited to, the first user device 2402, the second user device 2406, the third user device 2410, the fourth user device 2421, the fifth user device 2425, the earphone device 2430, the servers 2440, 2445, 2450, 2460, and the database 2455. The earphone device 2415 may also include any number of memories for storing content and/or instructions, processors that execute the instructions from the memories to perform the operations for the earphone device 2415, and/or any type integrated circuit for facilitating the operation of the earphone device 2415. In certain embodiments, the processors may comprise, hardware, software, or a combination of hardware and software. The earphone device 2415 may also include one or more ear canal receivers, which may be speakers for outputting sound into the ear canal of the first user 2401. The ear canal receivers may output sounds obtained via the ear canal microphones, ambient sound microphones, any of the devices in the system 2400, from a storage device of the earphone device 2415, or any combination thereof.

The ear canal receivers, ear canal microphones, transceivers, memories, processors, integrated circuits, and/or ear canal receivers may be affixed to an electronics package that includes a flexible electronics board. The earphone device 2415 may include an electronics packaging housing that may house the ambient sound microphones, ear canal microphones, ear canal receivers (i.e. speakers), electronics supporting the functionality of the microphones and/or receivers, transceivers for receiving and/or transmitting signals, power sources (e.g. batteries and the like), any circuitry facilitating the operation of the earphone device 2415, or any combination thereof. The electronics package including the flexible electronics board may be housed within the electronics packaging housing to form an electronics packaging unit. The earphone device 2415 may further include an earphone housing, which may include receptacles, openings, and/or keyed recesses for connecting the earphone housing to the electronics packaging housing and/or the electronics package. For example, nozzles of the electronics packaging housing may be inserted into one or more keyed recesses of the earphone housing so as to connect and secure the earphone housing to the electronics packaging housing. When the earphone housing is connected to the electronics packaging housing, the combination of the earphone housing and the electronics packaging housing may form the earphone device 2415. The earphone device 2415 may further include a cap for securing the electronics packaging housing, the earphone housing, and the electronics package together to form the earphone device 2415.

In certain embodiments, the earphone device 2415 may be configured to have any number of changeable tips, which may be utilized to facilitate the insertion of the earphone device 2415 into an ear aperture of an ear of the first user 2401, secure the earphone device 2415 within the ear canal of an ear of the first user 2401, and/or to isolate sound within the ear canal of the first user 2401. The tips may be foam tips, which may be affixed onto an end of the earphone housing of the earphone device 2415, such as onto a stent and/or attachment mechanism of the earphone housing. In certain embodiments, the tips may be any type of eartip as disclosed and described in the present disclosure. The eartips as disclosed in the present disclosure may be configured to facilitate distributed reduced contact force, sound isolation for sound in the ear canal of the first user 2401 (i.e. between the ambient environment and the ear canal environment within an ear of the first user 2401), mold into a variety of forms and/or positions, encapsulate volumes upon insertion into an ear aperture of the first user 2401, have a pressure adjusting design, facilitate notched stent retention (i.e. on a stent of the earphone housing), facilitate stent insertion into an ear canal of the first user 2401 via an ear aperture of the first user 2401, or any combination thereof. In certain embodiments, the eartip may be designed to provide sound isolation capability that is at least as effective as conventional foam and/or flange tips. Notably, the eartips may be manufactured and configured to be made in any desired size specifications and/or materials, and may be tailored to each individual user, such as first user 2401. In contrast to conventional foam or flange tips, an eartip according to the present disclosure may be adjusted for size without having to substitute the eartip with another eartip, may have an EPA NRR rating of NRR=18, may have a unique flatter high frequency attenuation profile so as to maintain audio quality, may have ease of manufacturability, and may be designed to distribute contact force and minimize radial force against a user's ear canal walls when positioned in a user's ear canal. Additionally, an eartip according to the present disclosure may be made of a non-porous material that is not closed cell foam or open cell foam.

In certain embodiments, the eartip may be designed so that the earphone device's 2415 retention force on the ear canal walls of the first user 2401 may be distributed over a larger area than traditional foam or flange tips allow, thereby reducing the pressure on the ear canal walls of the first user 2401. Unlike foam tips, which primarily provide a restoring radial force that exerts pressure against the ear canal walls of a user, the eartip is designed to move both radially and axially, which allows for more give and redistribution of contact over a larger area, and, thus, decreases the retention pressure. As a result, this allows for increased comfort for the user and allows the user to utilize the eartip for an extended period of time when compared to traditional foam and/or flange tips. In certain embodiments, the eartip utilized with the earphone device 2415 may be configured to encapsulate a volume of gas and/or liquid. In either case (i.e. gas or liquid), the bulk of sound isolation provided by the eartip is achieved through the reflection of ambient sound waves so that the encapsulated volume can be low mass. In certain embodiments, portions of the eartip may encapsulate a volume with the ability to release volume when pressed upon without having to incorporate complicated valves. The encapsulated volume may be achieved by the ear canal wall pressing radially and/or axially against the outer surfaces of the eartip, which may force the outer portion of the eartip to seal with the inner portion of the eartip. In certain embodiments, the inner portion of the eartip may be small than the outer diameter of the stent of the earphone housing upon which the eartip is placed so that upon insertion of the eartip on the stent, the inner portion stretches outward to meet the outer surface of the eartip, which further facilitates the sealing of the ear canal of the first user 2401.

In certain embodiments, the stent of the eartip, over which the eartip is placed, may be designed to have a smaller diameter front end and a larger diameter middle section to promote retention of the eartip on the stent itself. In certain embodiments, a portion of the eartip may have an inner core diameter that is smaller than the stent outer diameter so that the eartip provides radial compression upon the stent so as to enhance sealing and to add friction to prevent axial slippage within the ear canal of the first user 2401. In certain embodiments, an increased mid-section inner core diameter of the eartip may be utilized (i.e. larger than the smaller inner core diameter of the eartip), which may be configured to line up with the mid-section outer diameter of the stent of the earphone housing of the earphone device 2415. This may provide axial stability for the earphone device 2415, while simultaneously preventing axial slippage from the ear canal of the first user 2401. In certain embodiments, the eartip may have an insertion end that has a funnel shape, which aids in inserting the eartip onto the stent of the earphone housing of the earphone device 2415.

In certain embodiments, the eartip has a configuration that applies minimal force against the first user's 2401 ear canal. Additionally, the eartip can seal the first user's 2401 ear canal by providing at least 15 dB of attenuation across frequency. To facilitate manufacturability, the eartip may be molded inverted, thereby allowing inexpensive mass production. Lips of the eartip may then be folded to contact ledges to for the eartip that may be utilized by the first user 2401. Sealing and comfort depend upon an accurate fit within the first user's 2401 ear canal, and, as a result, eartips according to the present disclosure may be manufactured in several single sizes, and, because of the unique design of the eartips, a single eartip may be adjusted to fit multiple sizes, which minimizes manufacturing costs, while allowing for more flexibility, versatility, and for a greater number of sizes for the eartip. Notably, any of the features of any of the eartips described in the present disclosure may be combined and/or interchanged with any other eartips described in the present disclosure. Furthermore, the shape, size, features and/or functionality of any of the components of the earphone device and/or hearbud housing device described in the present disclosure may be modified for each particular user for the shape and size of each user's ear aperture and/or ear canal, or a combination thereof.

Notably, in experiments conducted using the eartip, the experiments have shown that the eartip allows for similar levels of sound isolation when compared to conventional foam and/or flange tips. For example, experiments have shown that the eartips provided in the present disclosure provided a NRR of 18 with a generally flat high frequency profile. A flat attenuation profile maintains an ambient environment's frequency profile when level reduced by the attenuation, which can be useful in maintaining the quality of ambient speech and music (or other audio content) during the level reduction process.

In further embodiments, the eartip may be configured to have an open configuration prior to insertion onto a stent of the earphone housing and/or the earphone device 2415 itself. By having an open configuration, the eartip may be mass produced using conventional molding techniques and/or by utilizing 3D commercial printers. The open configuration of the eartip also facilitates molding, and can be 3D printed, where the open configuration allows for resin removal. For example, resin removal may be achieved by utilizing commercial 3D printers that allow the use of lower durometer materials, such as Stratasys machines and the like. In certain embodiments, since the eartip has an open configuration, which is then sealed, any additional pressure can force encapsulated gas out of the eartip relieving the feedback pressure so as to keep the comfort level for the first user 2401 relatively stable.

In addition to the first user 2401, the system 2400 may include a second user 2420, who may utilize a fourth user device 2421 to access data, content, and applications, or to perform a variety of other tasks and functions. Much like the first user 2401, the second user 2420 may be may be any type of user that may potentially desire to listen to audio content, such as from, but not limited to, a storage device of the fourth user device 2421, a telephone call that the second user 2420 is participating in, audio content occurring in an environment in proximity to the second user 2420, any other type of audio content, or a combination thereof. For example, the second user 2420 may be an individual that may be listening to songs stored in a playlist that resides on the fourth user device 2421. Also, much like the first user 2401, the second user 2420 may utilize fourth user device 2421 to access an application (e.g. a browser or a mobile application) executing on the fourth user device 2421 that may be utilized to access web pages, data, and content associated with the system 2400. The fourth user device 2421 may include a memory 2422 that includes instructions, and a processor 2423 that executes the instructions from the memory 2422 to perform the various operations that are performed by the fourth user device 2421. In certain embodiments, the processor 2423 may be hardware, software, or a combination thereof. The fourth user device 2421 may also include an interface 2424 (e.g. a screen, a monitor, a graphical user interface, etc.) that may enable the second user 2420 to interact with various applications executing on the fourth user device 2421, to interact with various applications executing in the system 2400, and to interact with the system 2400. In certain embodiments, the fourth user device 2421 may include any number of transducers, such as, but not limited to, microphones, speakers, any type of audio-based transducer, any type of transducer, or a combination thereof. In certain embodiments, the fourth user device 2421 may be a computer, a laptop, a tablet device, a phablet, a server, a mobile device, a smartphone, a smart watch, and/or any other type of computing device. Illustratively, the fourth user device 2421 may be a computing device in FIG. 11. The fourth user device 2421 may also include any of the componentry described for first user device 2402, the second user device 2406, and/or the third user device 2410. In certain embodiments, the fourth user device 2421 may also include a global positioning system (GPS), which may include a GPS receiver and any other necessary components for enabling GPS functionality, accelerometers, gyroscopes, sensors, and any other componentry suitable for a computing device.

In addition to using fourth user device 2421, the second user 2420 may also utilize and/or have access to a fifth user device 2425. As with fourth user device 2421, the second user 2420 may utilize the fourth and fifth user devices 2421, 2425 to transmit signals to access various online services and content. The fifth user device 2425 may include a memory 2426 that includes instructions, and a processor 2427 that executes the instructions from the memory 2426 to perform the various operations that are performed by the fifth user device 2425. In certain embodiments, the processor 2427 may be hardware, software, or a combination thereof. The fifth user device 2425 may also include an interface 2428 that may enable the second user 2420 to interact with various applications executing on the fifth user device 2425 and to interact with the system 2400. In certain embodiments, the fifth user device 2425 may include any number of transducers, such as, but not limited to, microphones, speakers, any type of audio-based transducer, any type of transducer, or a combination thereof. In certain embodiments, the fifth user device 2425 may be and/or may include a computer, any type of sensor, a laptop, a set-top-box, a tablet device, a phablet, a server, a mobile device, a smartphone, a smart watch, and/or any other type of computing device. Illustratively, the fifth user device 2425 is shown as a tablet device in FIG. 11.

The fourth and fifth user devices 2421, 2425 may belong to and/or form a communications network 2431. In certain embodiments, the communications network 2431 may be a local, mesh, or other network that facilitates communications between the fourth and fifth user devices 2421, 2425, and/or any other devices, programs, and/or networks of system 2400 or outside system 2400. In certain embodiments, the communications network 2431 may be formed between the fourth and fifth user devices 2421, 2425 through the use of any type of wireless or other protocol and/or technology. For example, the fourth and fifth user devices 2421, 2425 may communicate with one another in the communications network 2416, such as by utilizing BLE, classic Bluetooth, ZigBee, cellular, NFC, Wi-Fi, Z-Wave, ANT+, IEEE 802.15.4, IEEE 802.22, ISA100a, infrared, ISM band, RFID, UWB, Wireless HD, Wireless USB, any other protocol and/or wireless technology, satellite, fiber, or any combination thereof. Notably, the communications network 2431 may be configured to communicatively link with and/or communicate with any other network of the system 2400 and/or outside the system 2400.

Much like first user 2401, the second user 2420 may have his or her own earphone device 2430. The earphone device 2430 may be utilized by the second user 2420 to hear and/or audition audio content, transmit audio content, receive audio content, experience any type of content, process audio content, adjust audio content, store audio content, perform any type of operation with respect to audio content, or a combination thereof. The earphone device 2430 may be an earpiece, a hearing aid, an ear monitor, an ear terminal, a behind-the-ear device, any type of acoustic device, or a combination thereof. The earphone device 2430 may include any type of component utilized for any type of earpiece, and may include any of the features, functionality and/or components described and/or usable with earphone device 2415. For example, earphone device 2430 may include any number of transceivers, ear canal microphones, ambient sound microphones, processors, memories, housings, eartips, foam tips, flanges, any other component, or any combination thereof.

In certain embodiments, the first, second, third, fourth, and/or fifth user devices 2402, 2406, 2410, 2421, 2425 and/or earphone devices 2415, 2430 may have any number of software applications and/or application services stored and/or accessible thereon. For example, the first and second user devices 2402, 2411 may include applications for processing audio content, applications for playing, editing, transmitting, and/or receiving audio content, streaming media applications, speech-to-text translation applications, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 2401, 2420 to readily interact with the software applications. The software applications and services may also be utilized by the first and second users 2401, 2420 to interact with any device in the system 2400, any network in the system 2400 (e.g. communications networks 2416, 2431, 2435), or any combination thereof. For example, the software applications executing on the first, second, third, fourth, and/or fifth user devices 2402, 2406, 2410, 2421, 2425 and/or earphone devices 2415, 2430 may be applications for receiving data, applications for storing data, applications for auditioning, editing, storing and/or processing audio content, applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first, second, third, fourth, and/or fifth user devices 2402, 2406, 2410, 2421, 2425 and/or earphone devices 2415, 2430 may include associated telephone numbers, internet protocol addresses, device identities, or any other identifiers to uniquely identify the first, second, third, fourth, and/or fifth user devices 2402, 2406, 2410, 2421, 2425 and/or earphone devices 2415, 2430 and/or the first and second users 2401, 2420. In certain embodiments, location information corresponding to the first, second, third, fourth, and/or fifth user devices 2402, 2406, 2410, 2421, 2425 and/or earphone devices 2415, 2430 may be obtained based on the internet protocol addresses, by receiving a signal from the first, second, third, fourth, and/or fifth user devices 2402, 2406, 2410, 2421, 2425 and/or earphone devices 2415, 2430 or based on profile information corresponding to the first, second, third, fourth, and/or fifth user devices 2402, 2406, 2410, 2421, 2425 and/or earphone devices 2415, 2430.

The system 2400 may also include a communications network 2435. The communications network 2435 may be under the control of a service provider, the first and/or second users 2401, 2420, any other designated user, or a combination thereof. The communications network 2435 of the system 2400 may be configured to link each of the devices in the system 2400 to one another. For example, the communications network 2435 may be utilized by the first user device 2402 to connect with other devices within or outside communications network 2435. Additionally, the communications network 2435 may be configured to transmit, generate, and receive any information and data traversing the system 2400. In certain embodiments, the communications network 2435 may include any number of servers, databases, or other componentry. The communications network 2435 may also include and be connected to a mesh network, a local network, a cloud-computing network, an IMS network, a VoIP network, a security network, a VoLTE network, a wireless network, an Ethernet network, a satellite network, a broadband network, a cellular network, a private network, a cable network, the Internet, an internet protocol network, MPLS network, a content distribution network, any network, or any combination thereof. Illustratively, servers 2440, 2445, and 2450 are shown as being included within communications network 2435. In certain embodiments, the communications network 2435 may be part of a single autonomous system that is located in a particular geographic region, or be part of multiple autonomous systems that span several geographic regions.

Notably, the functionality of the system 2400 may be supported and executed by using any combination of the servers 2440, 2445, 2450, and 2460. The servers 2440, 2445, and 2450 may reside in communications network 2435, however, in certain embodiments, the servers 2440, 2445, 2450 may reside outside communications network 2435. The servers 2440, 2445, and 2450 may provide and serve as a server service that performs the various operations and functions provided by the system 2400. In certain embodiments, the server 2440 may include a memory 2441 that includes instructions, and a processor 2442 that executes the instructions from the memory 2441 to perform various operations that are performed by the server 2440. The processor 2442 may be hardware, software, or a combination thereof. Similarly, the server 2445 may include a memory 2446 that includes instructions, and a processor 2447 that executes the instructions from the memory 2446 to perform the various operations that are performed by the server 2445. Furthermore, the server 2450 may include a memory 2451 that includes instructions, and a processor 2452 that executes the instructions from the memory 2451 to perform the various operations that are performed by the server 2450. In certain embodiments, the servers 2440, 2445, 2450, and 2460 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 2440, 2445, 2450 may be communicatively linked to the communications network 2435, the communications network 2416, the communications network 2431, any network, any device in the system 2400, any program in the system 2400, or any combination thereof.

The database 2455 of the system 2400 may be utilized to store and relay information that traverses the system 2400, cache content that traverses the system 2400, store data about each of the devices in the system 2400 and perform any other typical functions of a database. In certain embodiments, the database 2455 may be connected to or reside within the communications network 2435, the communications network 2416, the communications network 2431, any other network, or a combination thereof. In certain embodiments, the database 2455 may serve as a central repository for any information associated with any of the devices and information associated with the system 2400. Furthermore, the database 2455 may include a processor and memory or be connected to a processor and memory to perform the various operation associated with the database 2455. In certain embodiments, the database 2455 may be connected to the earphone devices 2415, 2430, the servers 2440, 2445, 2450, 2460, the first user device 2402, the second user device 2406, the third user device 2410, the fourth user device 2421, the fifth user device 2425, any devices in the system 2400, any other device, any network, or any combination thereof.

The database 2455 may also store information and metadata obtained from the system 2400, store metadata and other information associated with the first and second users 2401, 2420, store user profiles associated with the first and second users 2401, 2420, store device profiles associated with any device in the system 2400, store communications traversing the system 2400, store user preferences, store information associated with any device or signal in the system 2400, store information relating to patterns of usage relating to the first, second, third, fourth, and fifth user devices 2402, 2406, 2410, 2421, 2425, store audio content associated with the first, second, third, fourth, and fifth user devices 2402, 2406, 2410, 2421, 2425 and/or earphone devices 2415, 2430, store audio content and/or information associated with the audio content that is captured by the ambient sound microphones, store audio content and/or information associated with audio content that is captured by ear canal microphones, store any information obtained from any of the networks in the system 2400, store audio content and/or information associated with audio content that is outputted by ear canal receivers of the system 2400, store any information and/or signals transmitted and/or received by transceivers of the system 2400, store any device and/or capability specifications relating to the earphone devices 2415, 2430, store historical data associated with the first and second users 2401, 2415, store information relating to the size (e.g. depth, height, width, curvatures, etc.) and/or shape of the first and/or second user's 2401, 2420 ear canals and/or ears, store information identifying and or describing any eartip utilized with the earphone devices 2401, 2415, store device characteristics for any of the devices in the system 2400, store information relating to any devices associated with the first and second users 2401, 2420, store any information associated with the earphone devices 2415, 2430, store log on sequences and/or authentication information for accessing any of the devices of the system 2400, store information associated with the communications networks 2416, 2431, store any information generated and/or processed by the system 2400, store any of the information disclosed for any of the operations and functions disclosed for the system 2400 herewith, store any information traversing the system 2400, or any combination thereof. Furthermore, the database 2455 may be configured to process queries sent to it by any device in the system 2400.

The system 2400 may also include a software application, which may be configured to perform and support the operative functions of the system 2400, such as the operative functions of the first, second, third, fourth, and fifth user devices 2402, 2406, 2410, 2421, 2425 and/or the earphone devices 2415, 2430. In certain embodiments, the application may be a website, a mobile application, a software application, or a combination thereof, which may be made accessible to users utilizing one or more computing devices, such as the first, second, third, fourth, and fifth user devices 2402, 2406, 2410, 2421, 2425 and/or the earphone devices 2415, 2430. The application of the system 2400 may be accessible via an internet connection established with a browser program or other application executing on the first, second, third, fourth, and fifth user devices 2402, 2406, 2410, 2421, 2425 and/or the earphone devices 2415, 2430, a mobile application executing on the first, second, third, fourth, and fifth user devices 2402, 2406, 2410, 2421, 2425 and/or the earphone devices 2415, 2430, or through other suitable means. Additionally, the application may allow users and computing devices to create accounts with the application and sign-in to the created accounts with authenticating username and password log-in combinations. The application may include a custom graphical user interface that the first user 2401 or second user 2420 may interact with by utilizing a browser executing on the first, second, third, fourth, and fifth user devices 2402, 2406, 2410, 2421, 2425 and/or the earphone devices 2415, 2430. In certain embodiments, the software application may execute directly as an installed program on the first, second, third, fourth, and fifth user devices 2402, 2406, 2410, 2421, 2425 and/or the earphone devices 2415, 2430.

Computing System for Facilitating the Operation and Functionality of the System

Figure 12:
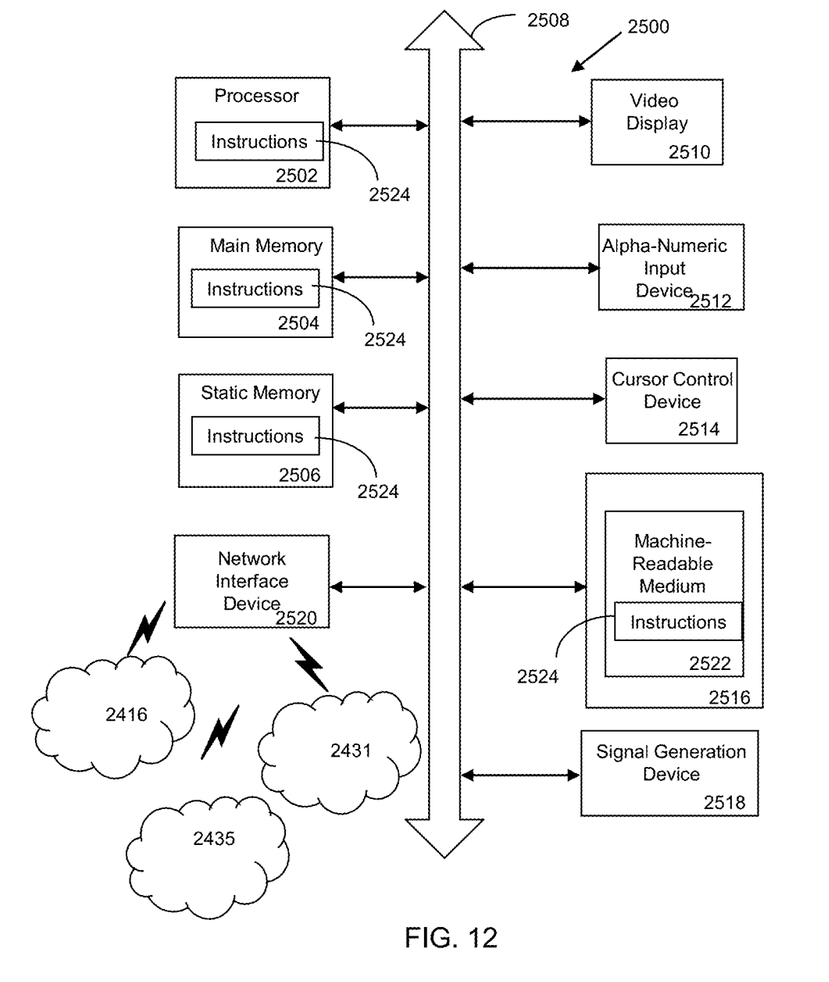
FIG. 12 is a schematic diagram of a machine in the form of a computer system which a set of instructions, when executed, may cause the machine to perform any one or more of the methodologies or operations of the systems and methods for utilizing an earphone according to embodiments of the present disclosure.

Referring now also to FIG. 12, at least a portion of the methodologies and techniques described with respect to the exemplary embodiments of the system 2400 can incorporate a machine, such as, but not limited to, computer system 2500, or other computing device within which a set of instructions, when executed, may cause the machine to perform any one or more of the methodologies or functions discussed above. The machine may be configured to facilitate various operations conducted by the system 2400. For example, the machine may be configured to, but is not limited to, assist the system 2400 by providing processing power to assist with processing loads experienced in the system 2400, by providing storage capacity for storing instructions or data traversing the system 2400, by providing functionality and/or programs for facilitating the operative functionality of the earphone devices 2415, 2430, and/or the first, second, third, fourth, and fifth user devices 2402, 2406, 2410, 2421, 2425 and/or the earphone devices 2415, 2430, by providing functionality and/or programs for facilitating operation of any of the components of the earphone devices 2415, 2430 (e.g. ear canal receivers, transceivers, ear canal microphones, ambient sound microphones, or by assisting with any other operations conducted by or within the system 2400.

In some embodiments, the machine may operate as a standalone device. In some embodiments, the machine may be connected (e.g., using communications network 2435, the communications network 2416, the communications network 2431, another network, or a combination thereof) to and assist with operations performed by other machines and systems, such as, but not limited to, the first user device 2402, the second user device 2411, the third user device 2410, the fourth user device 2421, the fifth user device 2425, the earphone device 2415, the earphone device 2430, the server 2440, the server 2450, the database 2455, the server 2460, or any combination thereof. The machine may be connected with any component in the system 2400. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 2500 may include a processor 2502 (e.g., a central processing unit (CPU), a graphics processing unit (GPU, or both), a main memory 2504 and a static memory 2506, which communicate with each other via a bus 2508. The computer system 2500 may further include a video display unit 2510, which may be, but is not limited to, a liquid crystal display (LCD), a flat panel, a solid state display, or a cathode ray tube (CRT). The computer system 2500 may include an input device 2512, such as, but not limited to, a keyboard, a cursor control device 2514, such as, but not limited to, a mouse, a disk drive unit 2516, a signal generation device 2518, such as, but not limited to, a speaker or remote control, and a network interface device 2520.

The disk drive unit 2516 may include a machine-readable medium 2522 on which is stored one or more sets of instructions 2524, such as, but not limited to, software embodying any one or more of the methodologies or functions described herein, including those methods illustrated above. The instructions 2524 may also reside, completely or at least partially, within the main memory 2504, the static memory 2506, or within the processor 2502, or a combination thereof, during execution thereof by the computer system 2500. The main memory 2504 and the processor 2502 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 2522 containing instructions 2524 so that a device connected to the communications network 2435, the communications network 2416, the communications network 2431, another network, or a combination thereof, can send or receive voice, video or data, and communicate over the communications network 2435, the communications network 2416, the communications network 2431, another network, or a combination thereof, using the instructions. The instructions 2524 may further be transmitted or received over the communications network 2435, another network, or a combination thereof, via the network interface device 2520.

While the machine-readable medium 2522 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

In at least one embodiment the step of measuring the vocalization of the user with an ear canal microphone and an ambient sound microphone refers to the microphone measuring the acoustic environment to which it is exposed, where the acoustic environment can include the user's voice or another's voice, and where the system 2400 can be configured to separate the user's voice from another's by comparing the ECM pickup with the ASM. For example, the ECM will primarily pickup the user's voice whose spectrum can be compared to the ASM pickup spectrum to separate out the user's voice in the ASM pickup from the ambient environment. For example, parsing the temporal signal from eth ECM and ASM into blocks, e.g., 256, and performing and FFT on the block, then looking at the amplitude and phase.

In at least one embodiment determining whether the user is in a noisy or quiet environment refers to measuring the SPL levels of the acoustic environment sampled by the ECM and ASM, and comparing the SPL levels to NIOSH and EPA standards for noise exposure, for example, a threshold level of 85 dB can be used as a threshold above which can be referred to as noisy, while a different lower level can be used to determine quiet, for example levels below 60 dB can be referred to as quiet. Note those these threshold values are non-limiting examples.

While the present invention has been described with reference to exemplary embodiments, it is to be understood that the invention is not limited to the disclosed exemplary embodiments. The scope of the following claims is to be accorded the broadest interpretation to encompass all modifications, equivalent structures and functions of the relevant exemplary embodiments. For example, if words such as "orthogonal", "perpendicular" are used, the intended meaning is "substantially orthogonal" and "substantially perpendicular" respectively. Additionally, although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. The device comprising:
   a user interface;
   a speaker that emits audio;
   a memory that stores instructions;
   a processor that executes the instructions to perform operations, the operations comprising:
   retrieving a first sentence audio content signal, wherein the first sentence audio content signal includes a non-musical first frequency band word (FBW1);
   retrieving a second sentence audio content signal, wherein the second sentence audio content signal includes a non-musical second frequency band word (FBW2), wherein the FBW1 and FBW2 are substantially orthogonal in frequency in time, wherein FBW1 and FBW2 are generated from the same sound source;

sending the first sentence audio content signal to the speaker to be emitted;

sending the second sentence audio content signal to the speaker to be emitted, wherein a portion of the first sentence audio content overlaps the second sentence audio content in time;

receiving a response from the user using the user interface; and storing the response into a machine readable medium.

2. The device according to claim 1, where the operations further include:

sending a list of questions visually to the user interface to stimulate the reception of a response, wherein the response indicates which of the following frequency band words have been heard FBW1 or FBW2 or both.

3. The device according to claim 1, wherein the user interface is a keyboard.

4. The device according to claim 1, wherein the user interface is a touch screen.

5. The device according to claim 1, wherein the user interface is a microphone.

6. The device according to claim 1, wherein the operations further comprise:

adjusting a first gain of the FBW1 and adjusting a second gain of the FBW2 based upon the response.

7. The device according to claim 6, wherein the first gain is increased if FBW1 is not indicated as being heard in the response by the user.

8. The device according to claim 6, wherein the second gain is increased if FBW2 is not indicated as being heard in the response by the user.

9. The device according to claim 6, wherein the first gain is decreased if FBW2 is not indicated as being heard in the response by the user.

10. The device according to claim 6, wherein the second gain is decreased if FBW1 is not indicated as being heard in the response by the user.

11. A method comprising:

retrieving a first sentence audio content signal, wherein the first sentence audio content signal includes a non-musical first frequency band word (FBW1);

retrieving a second sentence audio content signal, wherein the second sentence audio content signal includes a non-musical second frequency band word (FBW2), wherein the FBW1 and FBW2 are substantially orthogonal in frequency in time, wherein FBW1 and FBW2 are generated from the same sound source;

sending the first sentence audio content signal to the speaker to be emitted;

sending the second sentence audio content signal to the speaker to be emitted, wherein a portion of the first sentence audio content overlaps the second sentence audio content in time;

receiving a response from the user using a user interface; and storing the response into a machine readable medium.

12. The method according to claim 11, further comprising:

sending a list of questions visually to the user interface to stimulate the reception of a response, wherein the response indicates which of the following frequency band words have been heard FBW1 or FBW2 or both.

13. The method according to claim 12, further comprising:

adjusting a first gain of FBW1 and adjusting a second gain of FBW2 based upon the response.

14. The method according to claim 13, further comprising:

generating an adjusted FBW1 by applying the first gain to the FBW1;

generating an adjusted FBW2 by applying the second gain to the FBW2; and sending the adjusted FBW1 and adjusted FBW2 to the speaker.

15. The method according to claim 14, wherein the first gain and second gains are adjusted until a user indicates that they have heard both adjusted FBW1 and adjusted FBW2.

* * * * *